(12) United States Patent
Shimizu

(10) Patent No.: US 10,308,581 B2
(45) Date of Patent: *Jun. 4, 2019

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/542,855

(22) PCT Filed: May 25, 2017

(86) PCT No.: PCT/JP2017/019579
§ 371 (c)(1),
(2) Date: Jul. 11, 2017

(87) PCT Pub. No.: WO2018/179457
PCT Pub. Date: Oct. 4, 2018

(65) Prior Publication Data
US 2018/0282253 A1    Oct. 4, 2018

(30) Foreign Application Priority Data
Mar. 28, 2017   (JP) .................................. 2017-062764

(51) Int. Cl.
C07C 51/44    (2006.01)
C07C 51/12    (2006.01)
B01D 3/14     (2006.01)
B01D 3/00     (2006.01)

(52) U.S. Cl.
CPC ............. *C07C 51/12* (2013.01); *B01D 3/009* (2013.01); *B01D 3/143* (2013.01); *C07C 51/44* (2013.01)

(58) Field of Classification Search
USPC ....................................................... 562/519
See application file for complete search history.

(56) References Cited

U.S. PATENT DOCUMENTS

| | | |
|---|---|---|
| 5,756,836 A | 5/1998 | Shimizu et al. |
| 2009/0088587 A1 | 4/2009 | Powell |
| 2009/0270650 A1 | 10/2009 | Patt |
| 2011/0288333 A1 | 11/2011 | Shaver et al. |
| 2013/0281735 A1 | 10/2013 | Shimizu et al. |
| 2015/0025270 A1 | 1/2015 | Shimizu et al. |
| 2015/0299084 A1 | 10/2015 | Shimizu et al. |
| 2016/0137574 A1 | 5/2016 | Shaver et al. |
| 2016/0221917 A1 | 8/2016 | Scates et al. |

FOREIGN PATENT DOCUMENTS

| | | |
|---|---|---|
| EP | 0 687 662 A2 | 12/1995 |
| EP | 2 628 720 A1 | 8/2013 |
| EP | 2 653 458 A1 | 10/2013 |
| EP | 2 826 767 A1 | 1/2015 |
| EP | 2 937 329 A1 | 10/2015 |
| JP | 7-025813 A | 1/1995 |
| JP | 2001-508405 A | 6/2001 |
| JP | 2011-518880 A | 6/2011 |
| WO | WO 98/17619 A2 | 4/1998 |
| WO | WO 2009/042078 A1 | 4/2009 |
| WO | WO 2009/134333 A1 | 11/2009 |
| WO | WO 2011/146446 A1 | 11/2011 |
| WO | WO 2012/081418 A1 | 6/2012 |
| WO | WO 2013/137236 A1 | 9/2013 |
| WO | WO 2014/097867 A1 | 6/2014 |
| WO | WO 2016/076968 A1 | 5/2016 |
| WO | WO 2016/126292 A1 | 8/2016 |
| WO | WO 2016/194850 A1 | 12/2016 |

OTHER PUBLICATIONS

Extended European Search Report dated Feb. 12, 2018, in European Patent Application No. 17737197.8.
Written Opinion of the International Searching Authority and International Search Report (forms PCT/ISA/237 and PCT/ISA/210), dated Jul. 25, 2017, for corresponding International Application No. PCT/JP2017/019579.
English tranlsation of the Written Opinion dated Oct. 9, 2017, in PCT International Application No. PCT/JP2017/019579.
Japanese Notification of Reasons for Rejection for Application No. 2017-536046, dated Jul. 10, 2018, with English language translation.

*Primary Examiner* — Ana Z Muresan
(74) *Attorney, Agent, or Firm* — Birch, Stewart, Kolasch & Birch, LLP

(57) ABSTRACT

There is provided a method allowing industrially efficient production of high quality acetic acid having a good potassium permanganate test value and a low impurity content without a large cost.
The method for producing acetic acid according to the present invention has a carbonylation reaction step, an evaporation step and a lower boiling point component removal step, and wherein with heating of the evaporator, (i) an acetaldehyde concentration in the aqueous phase of an overhead condensate in a lower boiling point component removal column is controlled to not less than 2340 ppm by mass; and/or (ii) a methyl acetate concentration in the aqueous phase is controlled to less than 19.0% by mass and/or; (iii) a methyl acetate concentration in the organic phase of the overhead condensate in the lower boiling point component removal column is controlled to less than 38.0% by mass, and then at least a portion of the aqueous phase is treated in the acetaldehyde separation and removal step to recycle a residual liquid after the acetaldehyde separation and removal to the reaction vessel and/or the acetaldehyde separation and removal step and/or other processes.

10 Claims, 5 Drawing Sheets

[Figure 1]
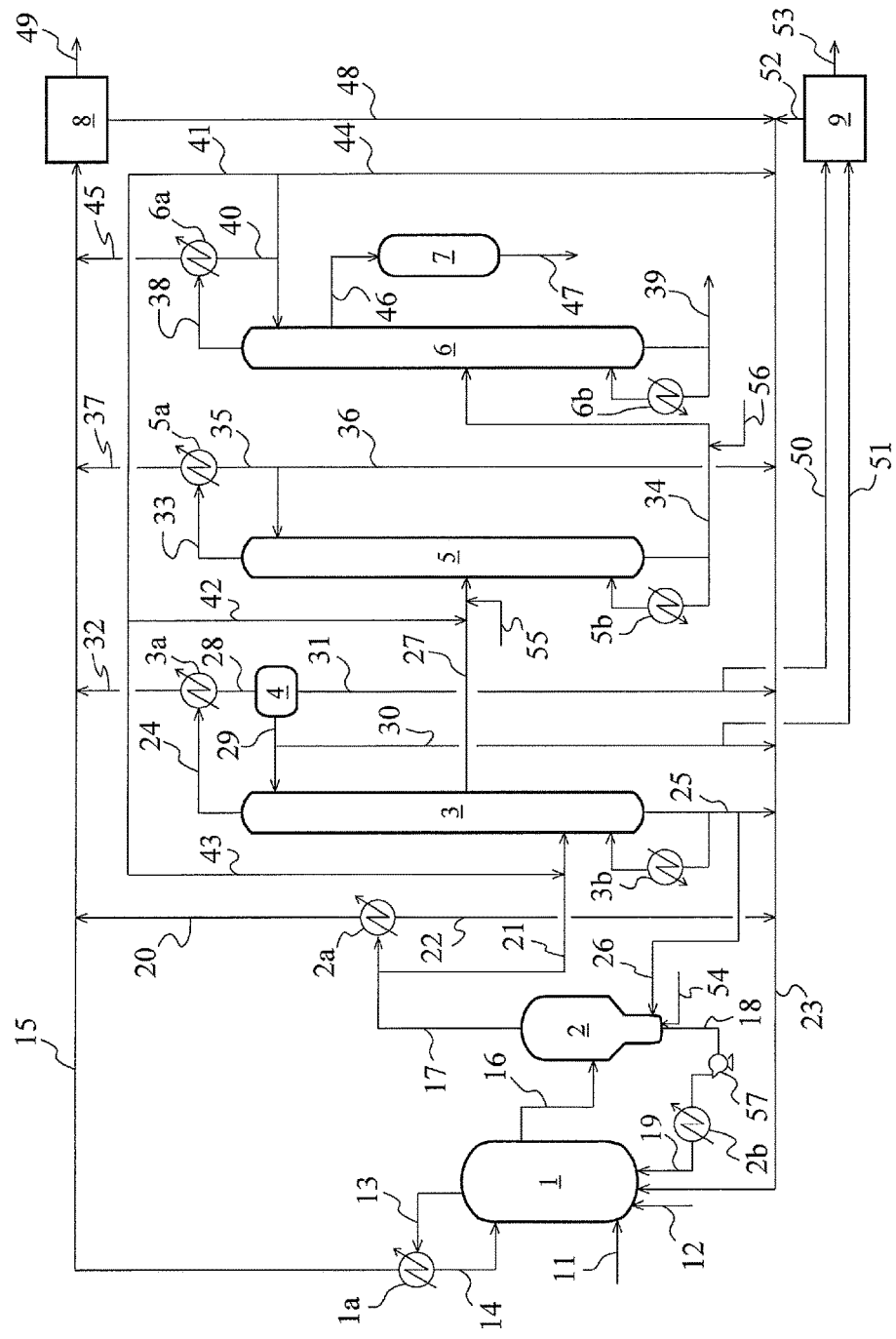

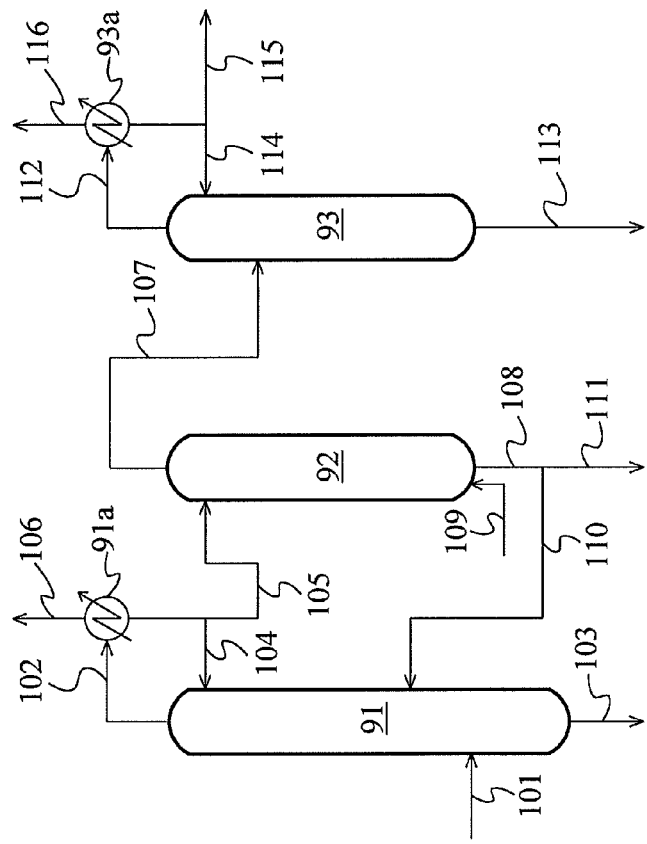
[Figure 2]

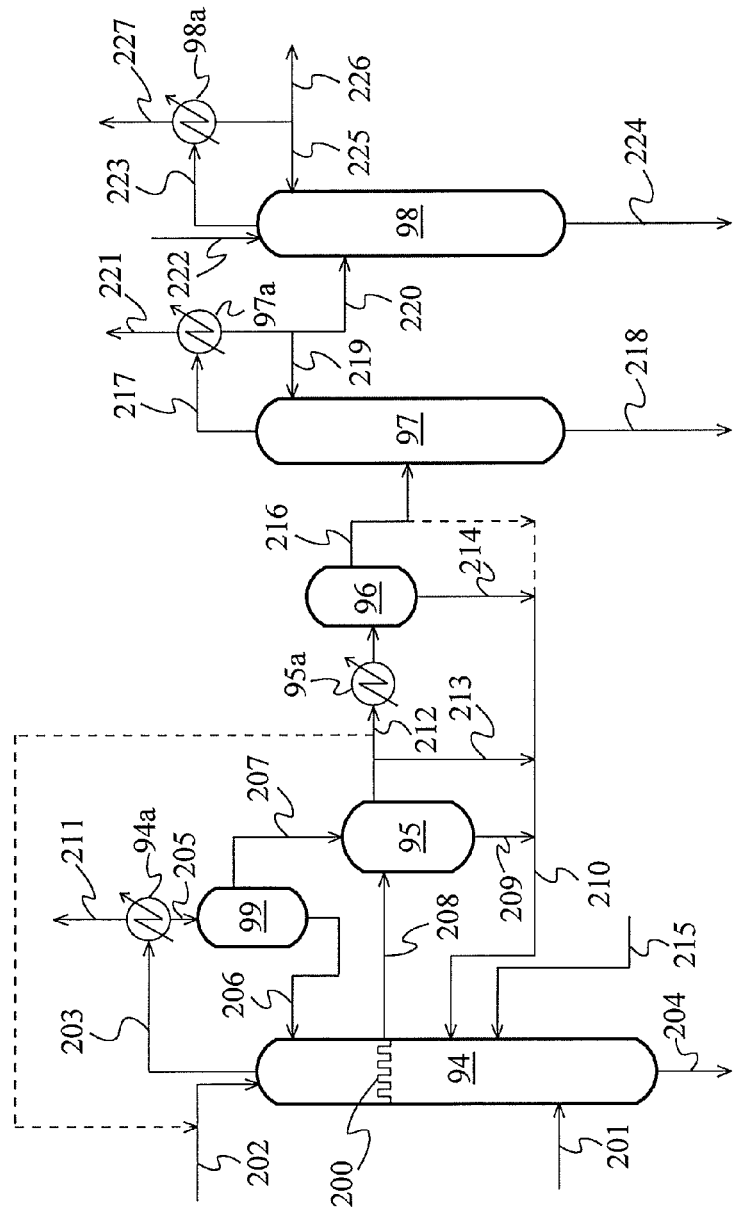
[Figure 3]

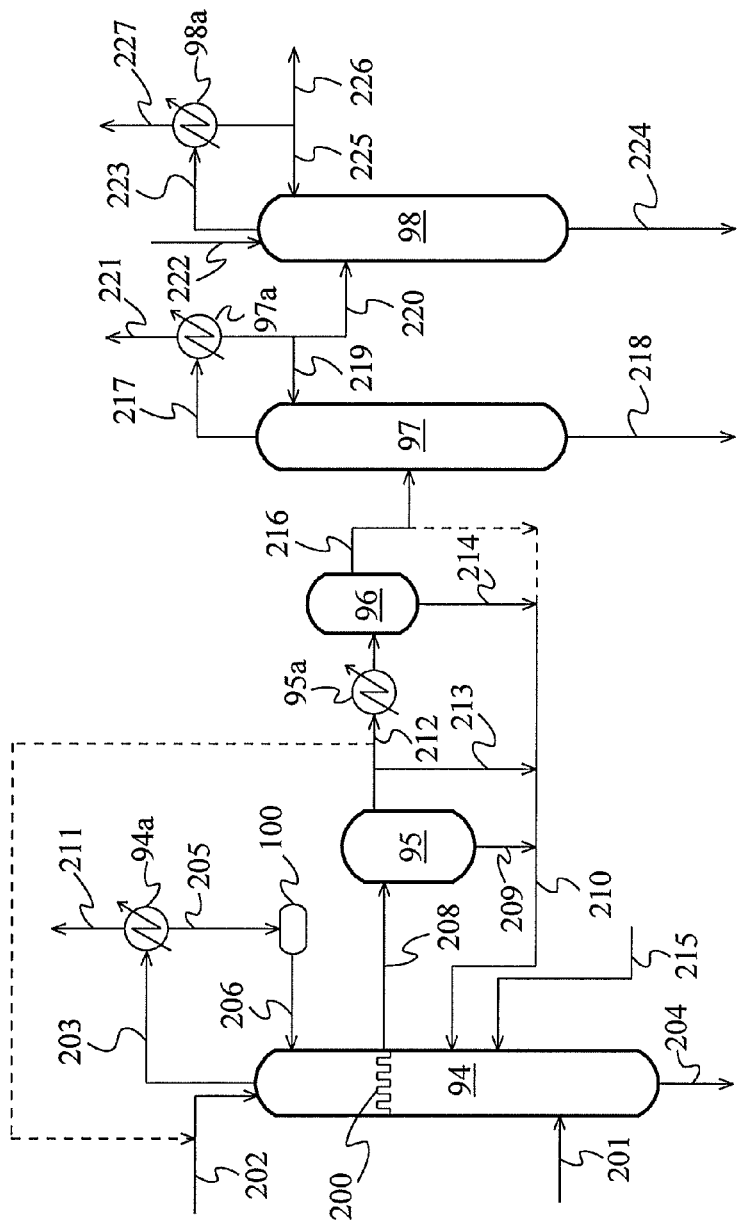
[Figure 4]

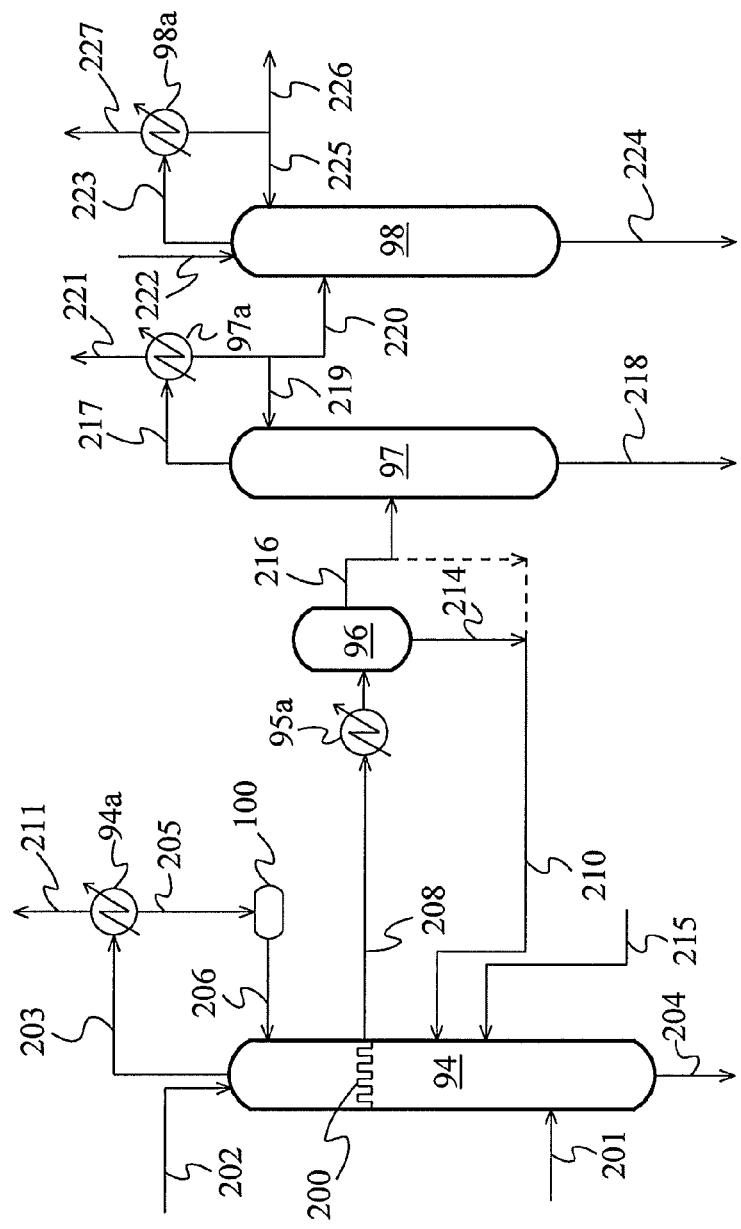
[Figure 5]

METHOD FOR PRODUCING ACETIC ACID

TECHNICAL FIELD

The present invention relates to a method for producing acetic acid. The present application claims the priority of Japanese Patent Application No. 2017-062764 filed in Japan on Mar. 28, 2017, the contents of which are incorporated herein by reference in their entirety.

BACKGROUND ART

A carbonylation process of a methanol method (methanol method acetic acid process) is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column.

In such an acetic acid production process, acetaldehyde generated by reduction of methyl iodide in the reaction system is converted into crotonaldehyde or 2-ethyl crotonaldehyde by aldol condensation, and thereby a potassium permanganate test value (permanganic acid time) of the product acetic acid is worsen. Moreover, after crotonaldehyde and acetaldehyde react, when hydrogen reduction and iodination is carried out, hexyl iodide is generated. If hexyl iodide is contained in the product acetic acid, a used palladium catalyst is deactivated in producing vinyl acetate using this acetic acid.

Conventionally, the two roughly classified methods have been adopted industrially in order to lower crotonaldehyde or 2-ethyl crotonaldehyde: (i) a method for suppressing generation of crotonaldehyde in a reaction system by removing acetaldehyde generated as a by-product in the reaction system from methyl iodide in the purification step and by lowering acetaldehyde in methyl iodide recycled to the reaction system; and (ii) a method of direct oxidative decomposition with ozone of crotonaldehyde contained in crude acetic acid obtained in the middle of a purification process (Patent Literatures 1 and 2). However, both separation and removal apparatus of acetaldehyde and ozonization apparatus are expensive. Until now, an improvement in the potassium permanganate test value of product acetic acid is extensively dependent on these methods to lead to an increase in apparatus cost. On the other hand, a method of treatment with a cation exchange resin substituted with a silver ion is known as a removal method of hexyl iodide. Meanwhile, in the treatment method using such a silver-substituted ion exchange resin, the silver-substituted ion exchange resin easily deteriorates to cause an increase in proportional cost. In National Publication of International Patent Application No. 2011-518880, a relationship of a flash temperature in case of introducing and heating reaction mixture of assumed composition in an evaporator with vapor and liquid composition discharged from a flasher is considered using a semiempirical simulator. However, this literature does not disclose or suggest that the acetaldehyde concentration and the methyl acetate concentration in the aqueous phase or the methyl acetate concentration in the organic phase of an overhead condensate obtained by subjecting vapor discharged from a flasher to a lower boiling point component removal column is controlled to decrease the concentrations of acetaldehyde, 2-ethyl crotonaldehyde and hexyl iodide in the reaction vessel.

CITATION LIST

Patent Literature

Patent Literature 1: Japan Patent Laid Open No. 07-25813
Patent Literature 2: National Publication of International Patent Application No. 2001-508405
Patent Literature 3: National Publication of International Patent Application No. 2011-518880

SUMMARY OF INVENTION

Technical Problem

Therefore, an object of the present invention is to provide a method allowing industrially efficient production of high quality acetic acid having a good potassium permanganate test value and a low impurity content without a large cost.

Solution to Problem

In order to attain the object, the present inventors have conducted diligent studies to discover that, in the methanol method carbonylation process, when the acetaldehyde concentration in evaporator bottom fraction is decreased by heating the evaporator and simultaneously an acetic acid concentration fed into a lower boiling point component removal column is increased, it is possible to control acetaldehyde distribution coefficient at the time of separating an overhead condensate in the lower boiling point component removal column into an aqueous phase and an organic phase so as to increase the amount of acetaldehyde distributed on the side of the aqueous phase and then the aqueous phase is subjected to an acetaldehyde removal treatment to allow for a great improvement in efficiency of acetaldehyde removal. The cause of the increase in acetaldehyde distribution coefficients is that the methyl acetate concentration of the distillation column overhead decreases by changes in distillation conditions due to a change in composition of the lower boiling point component removal column fed liquid, and this decrease in methyl acetate concentration affects the acetaldehyde distribution coefficient. The improvement in efficiency of acetaldehyde removal lowers the acetaldehyde concentration in the reaction mixture liquid of the reaction vessel to suppress the amounts of crotonaldehyde, 2-ethyl crotonaldehyde and hexyl iodide generated. When the acetaldehyde concentration in the reaction mixture liquid of the reaction vessel is lowered, there is also lowered generation of propionic acid due to the reaction: acetaldehyde+$H_2$+CO→propionic acid. It has found that when a reflux ratio of the lower boiling point component removal column is further increased, acetaldehyde is further concentrated in the column top to much more improve acetaldehyde removal efficiency. The present invention is based on these findings and has been completed through further studies.

Specifically, the present invention provides a method for producing acetic acid (hereinafter, sometimes referred to as a "first method for producing acetic acid"), comprising: a carbonylation reaction step of reacting methanol with carbon monoxide in a reaction vessel in the presence of a catalyst system containing a metal catalyst and methyl iodide as well as acetic acid, methyl acetate, and water to produce acetic acid;

an evaporation step of introducing and heating the reaction mixture obtained at the carbonylation reaction step in an evaporator to separate the reaction mixture into a vapor stream and a residual liquid stream;

a residual liquid stream recycle step of recycling the residual liquid stream to a reaction vessel;

a lower boiling point component removal step of separating the vapor stream with a first distillation column into a first overhead stream rich in methyl iodide and acetaldehyde and a first acetic acid stream rich in acetic acid and of condensing and separating the first overhead stream to obtain an aqueous phase and an organic phase; a first overhead stream recycle step of recycling at least a portion of the aqueous phase and/or the organic phase to the reaction vessel; and an acetaldehyde separation and removal step of separating and removing acetaldehyde in a process stream, wherein with heating of the evaporator, (i) the acetaldehyde concentration in the aqueous phase is controlled to not less than 2340 ppm by mass, and/or (ii) the methyl acetate concentration in the aqueous phase is controlled to less than 19.0% by mass, and/or (iii) the methyl acetate concentration in the organic phase is controlled to less than 38.0% by mass, and at least a portion of the aqueous phase is treated in the acetaldehyde separation and removal step, and a residual liquid after the acetaldehyde separation and removal is recycled to the reaction vessel and/or the acetaldehyde separation and removal step and/or other processes.

In the first method for producing acetic acid, the catalyst system may further contain ionic iodide.

As for operating conditions of the first distillation column, a reflux ratio of the aqueous phase may be not less than 2 when only the aqueous phase is refluxed to the first distillation column, a reflux ratio of the organic phase may be not less than 1 when only the organic phase is refluxed, and a total reflux ratio of the aqueous and organic phases may be not less than 1.5 when both the aqueous and organic phases are refluxed.

The first method for producing acetic acid may further comprise a dehydration step of separating the first acetic acid stream with a second distillation column into a second overhead stream rich in water and a second acetic acid stream richer in acetic acid than the first acetic acid stream. In this case, it is preferable that, in the second acetic acid stream, the crotonaldehyde concentration be not more than 1.10 ppm by mass and/or the 2-ethyl crotonaldehyde concentration be not more than 0.80 ppm by mass and/or the propionic acid concentration be not more than 130 ppm by mass.

In the first method for producing acetic acid, the acetaldehyde concentration of the residual liquid stream in the evaporator may be not more than 70 ppm by mass.

In the reaction mixture liquid of the reaction vessel, the crotonaldehyde concentration may be not more than 1.7 ppm by mass, and/or the 2-ethyl crotonaldehyde concentration may be not more than 1.8 ppm by mass, and/or the propionic acid concentration may be not more than 240 ppm by mass.

In the vapor stream fed to the first distillation column, the crotonaldehyde concentration may be not more than 2.4 ppm by mass, and/or the 2-ethyl crotonaldehyde concentration may be not more than 0.45 ppm by mass, and/or the propionic acid concentration may be not more than 106 ppm by mass.

In the first acetic acid stream, the crotonaldehyde concentration may be not more than 1.34 ppm by mass, and/or the 2-ethyl crotonaldehyde concentration may be not more than 0.60 ppm by mass, and/or the propionic acid concentration may be not more than 106 ppm by mass.

The present invention also provides a method for producing acetic acid (hereinafter, sometimes referred to as a "second method for producing acetic acid"), comprising: a carbonylation reaction step of reacting methanol with carbon monoxide in a reaction vessel in the presence of a catalyst system containing a metal catalyst and methyl iodide as well as acetic acid, methyl acetate, and water to produce acetic acid;

an evaporation step of introducing and heating the reaction mixture obtained in the carbonylation reaction step in an evaporator to separate the reaction mixture into a vapor stream and a residual liquid stream;

a residual liquid stream recycle step of recycling the residual liquid stream in the reaction vessel;

a lower boiling point component removal step of separating the vapor stream with a first distillation column into a first overhead stream rich in methyl iodide and acetaldehyde and a first acetic acid stream rich in acetic acid and of condensing and separating the first overhead stream to obtain an aqueous phase and an organic phase; a first overhead stream recycle step of recycling at least a portion of the aqueous phase and/or the organic phase to the reaction vessel; and an acetaldehyde separation and removal step of separating and removing acetaldehyde in a process stream, wherein with heating of the evaporator, (i) the acetaldehyde concentration in the aqueous phase is controlled to not less than 2340 ppm by mass, and/or (ii) the methyl acetate concentration in the aqueous phase is controlled to less than 19.0% by mass, and/or (iii) the methyl acetate concentration in the organic phase is controlled to less than 38.0% by mass, and an acetaldehyde concentration in the residual liquid stream is controlled to not more than 70 ppm by mass, at least a portion of the aqueous phase is treated in the acetaldehyde separation and removal step, and a residual liquid after the acetaldehyde separation and removal is recycled to the reaction vessel and/or the acetaldehyde separation and removal step and/or other processes, and a reflux ratio of the aqueous phase of the first distillation column is not less than 2.

In the second method for producing acetic acid, the catalyst system may further contain ionic iodide.

According to the present invention, with regard to the aqueous and organic phases obtained by heating the evaporator and separating the overhead condensate of the lower boiling point component removal column, since the acetaldehyde concentration of the aqueous phase and/or the methyl acetate concentration of the aqueous phase and/or the methyl acetate concentration of an organic phase are controlled within a specific range, an amount of acetaldehyde distributed on the side of the aqueous phase increases and therefore acetaldehyde can be efficiently separated and removed by subjecting this aqueous phase to the acetaldehyde separation and removal step. For this reason, the acetaldehyde concentration in the reaction vessel is lowered to suppress the amounts of crotonaldehyde, 2-ethyl crotonaldehyde, hexyl iodide and, in addition, propionic acid generated. Thus, even if a large-scale acetaldehyde removal apparatus or an ozonization apparatus is not disposed, high quality product acetic acid having a good potassium permanganate test value and little impurity content can be obtained. The effect will become still more remarkable by adjusting heating of the evaporator to set the acetaldehyde concentration in the evaporator residual liquid stream (bottom fraction) to not more than a specific value or to set a reflux ratio of the lower boiling point component removal column to not less than a specific value.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

The first method for producing acetic acid of the present invention comprises: a carbonylation reaction step of reacting methanol with carbon monoxide in a reaction vessel in the presence of a catalyst system containing a metal catalyst and methyl iodide as well as acetic acid, methyl acetate, and water to produce acetic acid; an evaporation step of introducing and heating the reaction mixture obtained in the carbonylation reaction step in an evaporator to separate the reaction mixture into a vapor stream and a residual liquid stream; a residual liquid stream recycle step of recycling the residual liquid stream in the reaction vessel; a lower boiling point component removal step of separating the vapor stream with a first distillation column into a first overhead stream rich in methyl iodide and acetaldehyde and a first acetic acid stream rich in acetic acid and of condensing and separating the first overhead stream to obtain an aqueous phase and an organic phase; a first overhead stream recycle step of recycling at least a portion of the aqueous phase and/or the organic phase to the reaction vessel; and an acetaldehyde separation and removal step of separating and removing acetaldehyde in a process stream. With heating of the evaporator, (i) the acetaldehyde concentration in the aqueous phase is controlled to not less than 2340 ppm by mass, and/or (ii) the methyl acetate concentration in the aqueous phase is controlled to less than 19.0% by mass, and/or (iii) the methyl acetate concentration in the organic phase is controlled to less than 38.0% by mass and, in addition, at least a portion of the aqueous phase is treated in the acetaldehyde separation and removal step to recycle a residual liquid after the acetaldehyde separation and removal to the reaction vessel and/or the acetaldehyde separation and removal step and/or other processes (preferably to at least the reaction vessel). When the acetaldehyde concentration in the aqueous phase, the methyl acetate concentration in the aqueous phase, or the methyl acetate concentration in the organic phase is controlled within the above-mentioned range, a distribution coefficient of acetaldehyde [{acetaldehyde concentration in the aqueous phase (% by mass)}/{acetaldehyde concentration of the organic phase (% by mass)}] is increased. Specifically, the amount of acetaldehyde distributed on the side of the aqueous phase is increased. Therefore, the separation and removal efficiency of acetaldehyde can be greatly improved by subjecting this aqueous phase to the acetaldehyde separation and removal step.

The second method for producing acetic acid of the present invention comprises the carbonylation reaction step, the evaporation step, the residual liquid stream recycle step, the lower boiling point component removal step, the first overhead stream recycling step and the acetaldehyde separation and removal step, which are mentioned above. With heating of the evaporator, (i) the acetaldehyde concentration in the aqueous phase is controlled to not less than 2340 ppm by mass, and/or (ii) the methyl acetate concentration in the aqueous phase is controlled to less than 19.0% by mass, and/or (iii) the methyl acetate concentration in the organic phase is controlled to less than 38.0% by mass, and the acetaldehyde concentration in the residual liquid stream is controlled to not more than 70 ppm by mass, at least a portion of the aqueous phase is treated in the acetaldehyde separation and removal step, and a residual liquid after the acetaldehyde separation and removal is recycled to the reaction vessel and/or the acetaldehyde separation and removal step and/or other processes (preferably to at least the reaction vessel), and, in addition, a reflux ratio of the aqueous phase of the first distillation column is not less than 2. The second method for producing acetic acid of the present invention is one of preferable aspects of the first method for producing acetic acid of the present invention.

In the above-mentioned (i), the acetaldehyde concentration in the aqueous phase is preferably not less than 2400 ppm by mass, more preferably not less than 2500 ppm by mass, and further preferably not less than 2600 ppm by mass. The upper limit of acetaldehyde concentration in the aqueous phase may be, for example, 1.0% by mass or 5000 ppm by mass. In the above-mentioned (ii), the methyl acetate concentration in the aqueous phase is preferably not more than 18.5% by mass, more preferably not more than 17.5% by mass, and further preferably not more than 17.0% by mass. The lower limit of methyl acetate concentration in the aqueous phase may be 1.0% by mass or 5.0% by mass (alternatively 8.0% by mass or 10.0% by mass). In the above-mentioned (iii), the methyl acetate concentration in the organic phase is preferably not more than 37.5% by mass, more preferably not more than 37.0% by mass, further preferably not more than 35.0% by mass, and particularly preferably not more than 30.0% by mass (for example, not more than 25.0% by mass). The lower limit of methyl acetate concentration in the organic phase may be, for example, 1.0% by mass or 2.0% by mass or may be 5.0% by mass (alternatively 10.0% by mass or 15.0% by mass, particularly 20.0% by mass).

In the first and second methods for producing acetic acid (hereafter, these may be generically named "the method for producing acetic acid according to the present invention"), the catalyst system may further contain ionic iodide. Ionic iodide functions as a co-catalyst.

In the method for producing acetic acid according to the present invention, at least a portion of the aqueous phase is treated in the acetaldehyde separation and removal step to recycle a residual liquid after the acetaldehyde separation and removal to the reaction vessel etc. and, in addition to this, at least a portion of the organic phase may be treated in the acetaldehyde separation and removal step to recycle the residual liquid after acetaldehyde separation and removal to the reaction vessel etc.

Moreover, the method for producing acetic acid according to the present invention may comprise a dehydration step for separating the first acetic acid stream with the second distillation column into a second overhead stream that is rich in water and a second acetic acid stream that is richer in acetic acid than the first acetic acid stream. The dehydration of the first acetic acid stream in the second distillation column provides the second acetic acid stream with little water content as a bottom fraction or a side cut liquid from the bottom or the middle of the column. The second acetic acid stream may be used as product acetic acid as it is or by further refinement if needed.

In the method for producing acetic acid according to the present invention, when only the aqueous phase of condensate of the first overhead stream is refluxed to the first distillation column, a reflux ratio of the aqueous phase (amount of the aqueous phase refluxed/amount of the distillate of the aqueous phase) is desirably, for example, not less than 2, preferably not less than 3, more preferably not less than 5, further preferably not less than 8, particularly preferably not less than 10 and, in particular, not less than 12. Also, when only the organic phase of condensate of the first overhead stream is refluxed to the first distillation column, a reflux ratio of the organic phase (amount of the organic phase refluxed/amount of the distillate of the organic phase) is desirably, for example, not less than 1, preferably not less than 1.5, more preferably not less than 2, further preferably not less than 4, and particularly preferably not less than 5. Moreover, when both the aqueous and organic phases of condensate of the first overhead stream are refluxed to the first distillation column, a total reflux ratio of the aqueous and organic phases (total amount of the aqueous and organic phases refluxed/total amount of the distillate of the aqueous and organic phases) is desirably, for example, not less than 1.5, preferably not less than 2.3, more preferably not less than 3.5, further preferably not less than 6, and particularly preferably not less than 8.5. Furthermore, when the aqueous phase is refluxed to the first distillation column, a reflux ratio of the aqueous phase (amount of the aqueous phase refluxed/amount of the distillate of the aqueous phase) is preferably not less than 2, more preferably not less than 3, further preferably not less than 5, particularly preferably not less than 8 and, in particular, not less than 12. In any case, the upper limit of the reflux ratio of the first distillation column may be, for example, 3000 (particularly 1000) or may be 100 (particularly 30). Since an increased reflux ratio of the first distillation column allows for concentrating acetaldehyde to the column top, acetaldehyde removal efficiency can be more improved by subjecting condensate of the column top to the acetaldehyde separation and removal step.

In the method for producing acetic acid according to the present invention, it is preferable to set an acetaldehyde concentration in the residual liquid stream (bottom fraction) in the evaporator to not more than 70 ppm by mass by adjusting heating of the evaporator. The acetaldehyde concentration in the residual liquid stream is more preferably not more than 60 ppm by mass, further preferably not more than 50 ppm by mass, and particularly preferably not more than 40 ppm by mass (e.g. not more than 30 ppm by mass). When such an operation is performed, since the residual liquid stream is recycled to the reaction vessel as a catalyst liquid, the amount of acetaldehyde recycled to the reaction vessel is decreased, and thereby it is possible to suppress generation of by-products such as crotonaldehyde, 2-ethyl crotonaldehyde, hexyl iodide and propionic acid in the reaction vessel.

In the method for producing acetic acid according to the present invention, since acetaldehyde separation and removal efficiency can be made high as mentioned above, the amount of acetaldehyde returned to the reaction system is decreased and, as the result, it is possible to lower the concentrations of crotonaldehyde 2-ethyl crotonaldehyde, propionic acid and a hexyl iodide in a reaction mixture liquid of the reaction vessel.

The crotonaldehyde concentration in the reaction mixture liquid of the reaction vessel is, for example, not more than 1.7 ppm by mass, preferably not more than 1.4 ppm by mass, more preferably not more than 1.2 ppm by mass, particularly preferably not more than 1.0 ppm by mass (e.g. not more than 0.8 ppm by mass and in particular not more than 0.6 ppm by mass). The lower limit of crotonaldehyde concentration in the reaction mixture liquid of the reaction vessel may be, for example, 0.01 ppm by mass (or 0.1 ppm by mass). The 2-ethyl crotonaldehyde concentration in the reaction mixture liquid of the reaction vessel is, for example, not more than 1.8 ppm by mass, preferably not more than 1.6 ppm by mass, more preferably not more than 1.4 ppm by mass, particularly preferably not more than 1.2 ppm by mass (e.g. not more than 1.0 ppm by mass and in particular not more than 0.8 ppm by mass). The lower limit of 2-ethyl crotonaldehyde concentration in the reaction mixture liquid of the reaction vessel may be, for example, 0.01 ppm by mass (or 0.1 ppm by mass). The propionic acid concentration in the reaction mixture liquid of the reaction vessel is, for example, not more than 240 ppm by mass, preferably not more than 230 ppm by mass, more preferably not more than 220 ppm by mass, and particularly preferably not more than 200 ppm by mass (e.g. not more than 180 ppm by mass). The lower limit of propionic acid concentration in the reaction mixture liquid of the reaction vessel may be, for example, 10 ppm by mass (or 50 ppm by mass).

When each concentration of crotonaldehyde, 2-ethyl crotonaldehyde, propionic acid and hexyl iodide is lowered in the reaction mixture liquid of the reaction vessel, the concentration of these impurities is lowered in the vapor stream fed to the first distillation column and also the concentration of these impurities is lowered in the first acetic acid stream further obtained from the first distillation column, and thereby high quality product acetic acid having a good potassium permanganate test value and a low concentration of these impurities can be obtained. For this reason, it is possible to downsize or omit an acetaldehyde removal apparatus and an ozonization apparatus that have been conventionally used for improving a potassium permanganate test value. Moreover, since acetic acid having a high potassium permanganate test value can be obtained by passing through only a lower boiling point component removal column or a dehydration column, it becomes possible to downsize or omit a subsequent higher boiling point component removal column or product column (finishing column).

The crotonaldehyde concentration in the vapor stream fed to the first distillation column is, for example, not more than 2.4 ppm by mass, preferably not more than 2.2 ppm by mass, more preferably not more than 2.0 ppm by mass, particularly preferably not more than 1.6 ppm by mass (e.g. not more than 1.2 ppm by mass). The lower limit of crotonaldehyde concentration in the vapor stream fed to the first distillation column may be, for example, 0.01 ppm by mass (or 0.1 ppm by mass). The 2-ethyl crotonaldehyde concentration in the vapor stream fed to the first distillation column is, for example, not more than 0.45 ppm by mass, preferably not more than 0.40 ppm by mass, more preferably not more than 0.30 ppm by mass. The lower limit of 2-ethyl crotonaldehyde concentration in the vapor stream fed to the first distillation column may be, for example, 0.01 ppm by mass (or 0.1 ppm by mass). The propionic acid concentration in the vapor stream fed to the first distillation column is, for example, not more than 106 ppm by mass, preferably not more than 74.0 ppm by mass, more preferably not more than 65.0 ppm by mass, and further preferably not more than 55.0 ppm by mass. The lower limit of propionic acid concentration in the vapor stream fed to the first distillation column may be, for example, 1.0 ppm by mass or may be 5.0 ppm by mass or 10.0 ppm by mass.

The crotonaldehyde concentration in the first acetic acid stream is, for example, not more than 1.34 ppm by mass, preferably not more than 1.20 ppm by mass, more preferably not more than 1.00 ppm by mass, further preferably not more than 0.80 ppm by mass, and particularly preferably not more than 0.60 ppm by mass. The lower limit of crotonaldehyde concentration in the first acetic acid stream may be, for example, 0.01 ppm by mass (or 0.05 ppm by mass). The 2-ethyl crotonaldehyde concentration in the first acetic acid stream is, for example, not more than 0.60 ppm by mass, preferably not more than 0.50 ppm by mass, more preferably not more than 0.40 ppm by mass. The lower limit of 2-ethyl crotonaldehyde concentration in the first acetic acid stream may be, for example, 0.01 ppm by mass (or 0.05 ppm by mass). The propionic acid concentration in the first acetic acid stream is, for example, not more than 106 ppm by mass, preferably not more than 100 ppm by mass, more preferably not more than 90.0 ppm by mass, and further preferably not more than 80.0 ppm by mass. The lower limit of propionic acid concentration in the first acetic acid stream may be, for example, 1.0 ppm by mass, or 5.0 ppm by mass or 10.0 ppm by mass.

The crotonaldehyde concentration in the second acetic acid stream obtained from the dehydration column is, for example, not more than 1.10 ppm by mass, preferably not more than 1.00 ppm by mass, more preferably not more than 0.90 ppm by mass, further preferably not more than 0.80 ppm by mass, and particularly preferably not more than 0.70 ppm by mass (e.g. not more than 0.60 ppm by mass). The lower limit of crotonaldehyde concentration in the second acetic acid stream may be, for example, 0.01 ppm by mass (or 0.05 ppm by mass). The 2-ethyl crotonaldehyde concentration in the second acetic acid stream is, for example, not more than 0.80 ppm by mass, preferably not more than 0.70 ppm by mass, more preferably not more than 0.60 ppm by mass, further preferably not more than 0.50 ppm by mass, and particularly preferably not more than 0.40 ppm by mass. The lower limit of 2-ethyl crotonaldehyde concentration in the second acetic acid stream may be, for example, 0.01 ppm by mass (or 0.05 ppm by mass). The propionic acid concentration in the second acetic acid stream is, for example, not more than 130 ppm by mass, preferably not more than 120 ppm by mass, more preferably not more than 110 ppm by mass, and further preferably not more than 80.0 ppm by mass. The lower limit of propionic acid concentration in the second acetic acid stream may be, for example, 1.0 ppm by mass or may be 5.0 ppm by mass or 10.0 ppm by mass. The hexyl iodide concentration in the second acetic acid stream is, for example, not more than 30 ppb by mass, preferably not more than 25 ppb by mass, more preferably not more than 20 ppb by mass, further preferably not more than 17 ppb by mass, and particularly preferably not more than 10 ppb by mass. The lower limit of hexyl iodide concentration in the second acetic acid stream may be, for example, 0.1 ppb by mass (or 1.0 ppb by mass).

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. In the present invention, the steps are not limited to those described above and may exclude, for example, equipment of the distillation column 5, the distillation column 6, the ion exchange resin column 7, the acetaldehyde separation and removal system 9 (acetaldehyde removal column, etc.). As mentioned later, a product column may be disposed downstream of the ion exchange resin column 7.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \tag{1}$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11.

Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^-$ can be used as the iridium catalyst. A metal complex catalyst is preferred as the metal catalyst. The concentration (in terms of the metal) of the catalyst in the reaction mixture is, for example, 100 to 10000 ppm by mass, preferably 200 to 5000 ppm by mass, further preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. Moreover, when, for example, an iridium catalyst or the like is used, a ruthenium compound and an osmium compound may also be used as a co-catalyst. The total usage of these compounds is, for example, 0.1 to 30 mol (metal conversion) and preferably 0.5 to 15 mol (metal conversion) per mol (metal conversion) of iridium.

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture.

Moreover, the by-products include, for example, hydrogen, methane, carbon dioxide, acetaldehyde, crotonaldehyde, 2-ethyl crotonaldehyde, butyl acetate, dimethyl ether, alkanes, formic acid, propionic acid, and alkyl iodides such as ethyl iodide, propyl iodide, butyl iodide, hexyl iodide and decyl iodide.

The acetaldehyde concentration in the reaction mixture liquid (liquid phase of the reaction mixture; reaction medium) is, for example, not more than 500 ppm by mass, preferably not more than 450 ppm by mass, more preferably not more than 400 ppm by mass, further preferably not more than 350 ppm by mass, and particularly preferably not more than 300 ppm by mass [e.g. not more than 250 ppm by mass (or not more than 210 ppm by mass)]. The lower limit of acetaldehyde concentration in the reaction mixture liquid is, for example, 1 ppm by mass (or 10 ppm by mass).

The crotonaldehyde concentration in the reaction mixture liquid is, for example, not more than 1.7 ppm by mass, preferably not more than 1.4 ppm by mass, more preferably not more than 1.2 ppm by mass, and particularly preferably not more than 1.0 ppm by mass (e.g. not more than 0.8 ppm by mass, in particular not more than 0.6 ppm by mass). The lower limit of crotonaldehyde concentration in the reaction mixture liquid is 0 ppm or may be, for example, 0.01 ppm by mass, 0.1 ppm by mass or 0.2 ppm by mass. The 2-ethyl crotonaldehyde concentration in the reaction mixture liquid is, for example, not more than 1.8 ppm by mass, preferably not more than 1.6 ppm by mass, more preferably not more than 1.4 ppm by mass, and particularly preferably not more than 1.2 ppm by mass (e.g. not more than 1.0 ppm by mass, in particular not more than 0.8 ppm by mass). The lower limit of 2-ethyl crotonaldehyde concentration in the reaction mixture liquid is 0 ppm or may be, for example, 0.01 ppm by mass or may be 0.1 ppm by mass or 0.2 ppm by mass. The propionic acid concentration in the reaction mixture liquid is, for example, not more than 240 ppm by mass, preferably not more than 230 ppm by mass, more preferably not more than 220 ppm by mass, and particularly preferably not more than 200 ppm by mass (e.g. not more than 180 ppm by mass). The lower limit of propionic acid concentration in the reaction mixture liquid is 0 ppm or may be, for example, 10 ppm by mass (or 50 ppm by mass).

Moreover, the reaction mixture liquid may contain a metal generated by corrosion of the apparatus [corroded metal (it is also called corrosion metal)] such as iron, nickel, chromium, manganese, molybdenum and other metals such as cobalt, zinc and copper. The above-mentioned corroded metal and other metals may be collectively called "corroded metal etc."

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.6 MPa (absolute pressure), further preferably 0.9 to 1.4 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. Hydrogen is contained in carbon monoxide used as a raw material and is also generated by a shift reaction ($CO+H_2O \rightarrow H_2+CO_2$) that occurs in the reaction vessel 1. The hydrogen partial pressure in the reaction vessel 1 is, for example, not less than 0.01 MPa (absolute pressure), preferably not less than 0.015 MPa (absolute pressure), more preferably not less than 0.02 MPa (absolute pressure), further preferably not less than 0.04 MPa (absolute pressure), and particularly preferably 0.06 MPa (absolute pressure) [e.g. not less than 0.07 MPa (absolute pressure)]. The upper limit of hydrogen partial pressure of the reaction vessel is, for example, 0.5 MPa (absolute pressure) [particularly 0.2 MPa (absolute pressure)]. The vapor of a gaseous phase portion in the reaction vessel 1 can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. In the present invention, the evaporation is caused by reducing the pressure while heating the evaporator. In the evaporation step, the temperature of the vapor stream is, for example, 100 to 260° C. and preferably 120 to 200° C., and the temperature of the residual liquid stream is, for example, 100 to 260° C. and preferably 120 to 200° C. The internal pressure of the evaporator is, for example, 50 to 1000 kPa (absolute pressure). The ratio between the vapor stream and the residual liquid stream to be separated in the evaporation step (vapor stream/residual liquid stream) is, for example, 10/90 to 60/40 in terms of a mass ratio (evaporation rate: 10 to 60% by mass), preferably 26/74 to 45/55 (evaporation rate: 26 to 45% by mass), more preferably 27/73 to 42/58 (evaporation rate: 27 to 42% by mass), and further preferably 30/70 to 40/60 (evaporation rate: 30 to 40% by mass).

The vapor generated in this step contains, for example, methyl iodide, hydrogen iodide, water, methyl acetate, acetic acid, dimethyl ether, methanol, acetaldehyde, crotonaldehyde, 2-ethyl crotonaldehyde, butyl acetate, formic acid, propionic acid and alkyl iodides such as ethyl iodide, propyl iodide, butyl iodide, hexyl iodide and decyl iodide, and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21.

The acetic acid concentration in the vapor stream is, for example, 50.0 to 90.0% by mass and preferably 55.0 to 85.0% by mass. The lower limit of acetic acid concentration is more preferably 57.0% by mass and further preferably 58.0% by mass (or 60.0% by mass, or 63.0% by mass, particularly 65.0% by mass) while the upper limit is more preferably 80.0% by mass, further preferably 75.0% by mass, and particularly preferably 72.0% by mass (or 68.0% by mass, or 65.5% by mass). A range of the acetic acid concentration is more preferably 57.0 to 68.0% by mass (for example, 58.0 to 65.5% by mass). The methyl iodide concentration of the vapor stream is, for example, 2.0 to 50.0% by mass, preferably 5.0 to 40.0% by mass. The lower limit of methyl iodide concentration is more preferably 10.0% by mass, further preferably 15% by mass, and particularly preferably 18.0% by mass (or 20.0% by mass, or 22.5% by mass) while the upper limit is more preferably 35.0% by mass, further preferably 30.0% by mass, and particularly preferably 28.0% by mass. A range of the methyl iodide concentration is more preferably 20.0 to 35.0% by mass (for example, 22.5 to 30.0% by mass). The water concentration in the vapor stream is, for example, 0.2 to 20.0% by mass, preferably 0.5 to 15.0% by mass, and more preferably 0.8 to 5.0% by mass. The lower limit of water concentration is more preferably 1.0% by mass and further preferably 1.2% by mass while the upper limit is more preferably 4.0% by mass and particularly preferably 3.0% by mass. A range of the water concentration is more preferably 1.2 to 5.0% by mass (for example, 1.2 to 4.0% by mass or 1.2 to 3.0% by mass). The methyl acetate concentration in the vapor stream is, for example, 0.2 to 50.0% by mass and preferably 2.0 to 30.0% by mass. The lower limit of methyl acetate concentration is more preferably 3.0% by mass, further preferably 5.0% by mass, and particularly preferably 6.0% by mass (or 7.0% by mass or 8.0% by mass) while the upper limit is more preferably 25.0% by mass, further preferably 20.0% by mass, and particularly preferably 15.0% by mass (or 10.0% by mass). A range of the methyl acetate concentration is more preferably 7.0 to 25.0% by mass (for example, 8.0 to 20.0% by mass).

The crotonaldehyde concentration in the vapor stream is, for example, not more than 2.4 ppm by mass, preferably not more than 2.2 ppm by mass, more preferably not more than 2.0 ppm by mass, and particularly preferably not more than 1.6 ppm by mass (e.g. not more than 1.2 ppm by mass). The lower limit of crotonaldehyde concentration in the vapor stream may be, for example, 0.01 ppm by mass (or 0.1 ppm by mass). The 2-ethyl crotonaldehyde concentration in the vapor stream liquid is, for example, not more than 0.45 ppm by mass, preferably not more than 0.40 ppm by mass, and more preferably not more than 0.30 ppm by mass. The lower limit of 2-ethyl crotonaldehyde concentration in the vapor stream may be, for example, 0.01 ppm by mass (or 0.1 ppm by mass). The propionic acid concentration in the vapor stream is, for example, not more than 106 ppm by mass, preferably not more than 74.0 ppm by mass, more preferably not more than 60.0 ppm by mass, and further preferably not more than 55.0 ppm by mass. The lower limit of propionic acid concentration in the vapor stream may be, for example, 1.0 ppm by mass or may be 5.0 ppm by mass or 10.0 ppm by mass.

The residual liquid stream generated in this step contains, for example, the catalyst and the co-catalyst (methyl iodide, lithium iodide, etc.) contained in the reaction mixture and contains water, acetaldehyde, methyl acetate, acetic acid, crotonaldehyde, 2-ethyl crotonaldehyde, butyl acetate, formic acid, propionic acid remaining without being volatilized in this step, and is continuously introduced to the heat exchanger $2b$ from the evaporator 2 through the line 18 using the pump 57. The acetaldehyde concentration in the residual liquid stream is preferably not more than 70 ppm by mass, more preferably not more than 60 ppm by mass, further preferably not more than 50 ppm by mass, and particularly preferably not more than 40 ppm by mass (for example, not more than 30 ppm by mass). When the acetaldehyde concentration in the residual liquid stream is lowered, generation of by-products such as crotonaldehyde, 2-ethyl crotonaldehyde, hexyl iodide and propionic acid in the reaction vessel 1 can be suppressed.

The heat exchanger $2b$ cools the residual liquid stream from the evaporator 2. The cooled residual liquid stream is continuously introduced to the reaction vessel 1 from the heat exchanger $2b$ through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser $2a$ separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, crotonaldehyde, 2-ethyl crotonaldehyde, butyl acetate, formic acid, and propionic acid and is introduced to the reaction vessel 1 from the condenser $2a$ through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser $2a$ through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser $2a$ is recycled to the reaction vessel 1. Specifically, in this acetic acid production apparatus, heat generated through the methanol carbonylation reaction is efficiently removed in the condenser $2a$.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50.

In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.)

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. $3b$ denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, crotonaldehyde and formic acid. This vapor also contains acetic acid. Such a vapor is continuously introduced to the condenser $3a$ through the line 24.

The condenser $3a$ separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, crotonaldehyde and formic acid and is continuously introduced to the decanter 4 from the condenser $3a$ through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, crotonaldehyde and formic acid. The organic phase contains, for example, methyl iodide and, for example, hydrogen iodide, water, methyl acetate, acetic acid, dimethyl ether, methanol, acetaldehyde, crotonaldehyde and formic acid.

As described above, in the producing method of the present invention, an evaporator is heated and (i) the acetaldehyde concentration in the aqueous phase is controlled to not less than 2340 ppm by mass and/or (ii) the methyl acetate concentration in the aqueous phase is controlled to less than 19.0% by mass and/or (iii) the methyl acetate concentration in the organic phase is controlled to less than 38.0% by mass and, in addition, at least a portion of the aqueous phase is treated in the acetaldehyde separation and removal step to recycle a residual liquid after the acetaldehyde separation and removal to a reaction vessel.

In the above-mentioned (i), the acetaldehyde concentration in the aqueous phase is preferably not less than 2400 ppm by mass, more preferably not less than 2500 ppm by mass, and further preferably not less than 2600 ppm by mass. The upper limit of acetaldehyde concentration in the aqueous phase may be, for example, 1.0% by mass or 5000 ppm by mass. In the above-mentioned (ii), the methyl acetate concentration in the aqueous phase is preferably not more than 18.5% by mass, more preferably not more than 17.5% by mass, and further preferably not more than 17.0% by mass. The lower limit of methyl acetate concentration in the aqueous phase may be, for example, 1.0% by mass or 5.0% by mass or may be 8.0% by mass or 10.0% by mass. In the above-mentioned (iii), the methyl acetate concentration in the organic phase is preferably not more than 37.5% by mass, more preferably 37.0% by mass, further preferably not more than 35.0% by mass, and particularly preferably not more than 30.0% by mass (e.g. not more than 25.0% by mass). The lower limit of methyl acetate concentration in the organic phase may be, for example, 1.0% by mass, 2.0% by mass, or 5.0% by mass or 10.0% by mass or may be 15.0% by mass (e.g. 20.0% by mass).

When the acetaldehyde concentration in the aqueous phase, the methyl acetate concentration in the aqueous phase or the methyl acetate concentration in the organic phase is within the above-mentioned range, the amount of acetaldehyde distributed on the side of the aqueous phase is increased. Therefore, separation and removal efficiency of acetaldehyde can be greatly improved by subjecting this aqueous phase to the acetaldehyde separation and removal step.

In the present embodiment, a portion of the aqueous phase is refluxed to the distillation column 3 through the line 29, and another portion of the aqueous phase is introduced to the acetaldehyde separation and removal system 9 through the lines 29, 30, and 51 to separate and remove acetaldehyde from the line 53 to the outside of the system. The residual liquid after the acetaldehyde separation and removal is recycled to the reaction vessel 1 through the lines 52 and 23. Another portion of the aqueous phase may be recycled to the reaction vessel 1 through lines 29, 30, and 23 without passing through the acetaldehyde separation and removal system 9. The organic phase is introduced into the reaction vessel 1 through the lines 31 and 23 and recycled. A portion of the organic phase may be, if necessary, introduced to the acetaldehyde separation and removal system 9 through the lines 31 and 50. In addition to or instead of the reflux of the aqueous phase to the distillation column 3, the organic phase may be refluxed to the distillation column 3.

A reflux ratio of the distillation column 3 is explained below. When only the aqueous phase of condensate of the first overhead stream is refluxed to the distillation column 3, a reflux ratio of the aqueous phase (amount of the aqueous phase refluxed/amount of the distillate of the aqueous phase) is desirably, for example, not less than 2, preferably not less than 3, more preferably not less than 5, further preferably not less than 8, and particularly preferably not less than 10 (e.g. not less than 12). When only the organic phase of condensate of the first overhead stream is refluxed to the distillation column 3, a reflux ratio of the organic phase (amount of the organic phase refluxed/amount of the distillate of the organic phase) is desirably, for example, not less than 1, preferably not less than 1.5, more preferably not less than 2, further preferably not less than 4, and particularly preferably not less than 5. Moreover, when both the aqueous and organic phases of condensate of the first overhead stream are refluxed to the distillation column 3, a total reflux ratio of the aqueous and organic phases (total amount of the aqueous and organic phases refluxed/total amount of the distillate of the aqueous and organic phases) is desirably, for example, not less than 1.5, preferably not less than 2.3, more preferably not less than 3.5, further preferably not less than 6, and particularly preferably not less than 8.5. Also, when the aqueous phase is refluxed to the distillation column 3, a reflux ratio of the aqueous phase (amount of the aqueous phase refluxed/amount of the distillate of the aqueous phase) is preferably not less than 2, more preferably not less than 3, further preferably not less than 5, and particularly preferably not less than 8, in particular, not less than 12. In any case, the upper limit of reflux ratio of the first distillation column may be, for example, 3000 (particularly 1000) or may be 100 (particularly 30). Since acetaldehyde can be condensed to the column top by raising a reflux ratio of the first distillation column, acetaldehyde removal efficiency can be more improved by subjecting the condensate of column top to the acetaldehyde separation and removal step.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97a through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98a through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94a through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94a, 97a, or 98a (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

In FIG. 1 described above, the gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, 2-ethyl crotonaldehyde, butyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90.0 to 99.9% by mass, preferably 93.0 to 99.0% by mass. In addition to acetic acid, the first acetic acid stream also contains, for example, methyl iodide, hydrogen iodide, water, methyl acetate, dimethyl ether, methanol, acetaldehyde, crotonaldehyde, 2-ethyl crotonaldehyde, butyl acetate, formic acid, propionic acid, and alkyl iodides such as ethyl iodide, propyl iodide, butyl iodide, hexyl iodide and decyl iodide.

In the first acetic acid stream, a methyl iodide concentration is, for example, 0.1 to 18% by mass (e.g. 0.1 to 8% by mass) and preferably 0.2 to 13% by mass (e.g. 0.2 to 5% by mass), a water concentration is, for example, 0.1 to 8% by mass and preferably 0.2 to 5% by mass, and the methyl acetate concentration is, for example, 0.1 to 8% by mass and preferably 0.2 to 5% by mass. Moreover, the crotonaldehyde concentration in the first acetic acid stream is, for example, not more than 1.34 ppm by mass, preferably not more than 1.20 ppm by mass, more preferably not more than 1.00 ppm by mass, further preferably not more than 0.80 ppm by mass, and particularly preferably not more than 0.60 ppm by mass. The lower limit of crotonaldehyde concentration in the first acetic acid stream may be, for example, 0.01 ppm by mass or 0.05 ppm by mass. The 2-ethyl crotonaldehyde concentration in the first acetic acid stream is, for example, not more than 0.60 ppm by mass, preferably not more than 0.50 ppm by mass, and more preferably not more than 0.40 ppm by mass. The lower limit of 2-ethyl crotonaldehyde concentration in the first acetic acid stream may be, for example, 0.01 ppm by mass or 0.05 ppm by mass. The propionic acid concentration in the first acetic acid stream is, for example, not more than 106 ppm by mass, preferably not more than 100 ppm by mass, more preferably not more than 90.0 ppm by mass, and further preferably not more than 80.0 ppm by mass. The lower limit of propionic acid concentration in the first acetic acid stream may be, for example, 1.0 ppm by mass or may be 5.0 ppm by mass or 10.0 ppm by mass.

The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27.

When the bottom fraction withdrawn from the column bottom of the distillation column 3 or the first acetic acid stream withdrawn from the distillation column 3 as a side stream has acceptable quality, it can be product acetic acid as it is.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. A material (material of at least a liquid contact part and a gas contact part) of the distillation column 5 is preferably a nickel based alloy or zirconium. In case of using such a material, corrosion of the inside of the distillation column due to hydrogen iodide or acetic acid can be suppressed, and elution of a corroded metal ion can be suppressed.

A charging mixture for the distillation column 5 contains at least a portion of the first acetic acid stream (line 27) and a stream other than the first acetic acid stream [for example, recycle stream from the downstream step (e.g. line 42)] may be added.

The distillation column 5 is composed of, for example, a distillation column such as a plate column or a packed column. In the case of adopting a plate column as the distillation column 5, the theoretical number of plates thereof is, for example, 5 to 50. The reflux ratio is optionally selected from not less than 0.2 according to the theoretical number of plates and is preferably not less than 0.3, more preferably not less than 0.35 and further preferably not less than 0.4. The upper limit of reflux ratio of the distillation column 5 is, for example, a 3000 (especially 1000) or may be 100 or approximately 10.

In the inside of the distillation column 5 in the second distillation step, the column top pressure is, for example, 0.10 to 0.28 MPa (gauge pressure), preferably 0.15 to 0.23 MPa (gage pressure) and further preferably 0.17 to 0.21 MPa (gage pressure). The column bottom pressure is higher than the column top pressure and is, for example, 0.13 to 0.31 MPa (gage pressure), preferably 0.18 to 0.26 MPa (gage pressure) and further preferably 0.20 to 0.24 MPa (gage pressure). In the inside of the distillation column 5 in the second distillation step, it is preferable that the column top temperature be less than 165° C. and the column bottom temperature be less than 175° C. When the column top temperature and column bottom temperature of the distillation column 5 are set to the above-mentioned range, corrosion of the inside of the distillation column due to hydrogen iodide or acetic acid can be more suppressed, and elution of corroded metal ions can be more suppressed. The column top temperature is more preferably less than 163° C., further preferably less than 161° C., particularly preferably less than 160° C. and, in particular, preferably less than 155° C. The lower limit of column top temperature is, for example, 110° C. The column bottom temperature is more preferably less than 173° C., further preferably less than 171° C. and particularly preferably less than 166° C. The lower limit of column bottom temperature is, for example, 120° C.

A vapor as an overhead stream (a second overhead stream) is continuously withdrawn to the line 33 from the column top of the distillation column 5. A bottom fraction is continuously withdrawn to the line 34 from the column bottom of the distillation column 5. 5*b* denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, crotonaldehyde and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

A bottom fraction withdrawn from the column bottom of the distillation column 5 or the side stream (second acetic acid stream) withdrawn from the middle part of the column is more enriched with acetic acid than the first acetic acid stream continuously introduced into the distillation column 5. Specifically, the acetic acid concentration of the second acetic acid stream is higher than the acetic acid concentration of the first acetic acid stream. The acetic acid concentration of the second acetic acid stream is, for example, 99.10 to 99.99% by mass as long as being higher than the acetic acid concentration of the first acetic acid stream. In the present embodiment, in the case of withdrawing a side stream, the withdrawal position of the side stream from the distillation column 5 is lower than the introduction position of the first acetic acid stream to the distillation column 5 in the height direction of the distillation column 5.

In the present invention, the second acetic acid stream has a high potassium permanganate test value and therefore can be product acetic acid as it is. However, the second acetic acid stream may contain a very small amount of impurities [for example, crotonaldehyde, 2-ethyl crotonaldehyde, butyl acetate, propionic acid, potassium acetate (when potassium hydroxide is fed to the line 27 etc.), hydrogen iodide, and the entrained catalyst and co-catalyst mentioned above]. Thus, such a bottom fraction or a side stream may be continuously introduced to the distillation column 6 through the line 34 and distilled.

The crotonaldehyde concentration in the second acetic acid stream is, for example, not more than 1.10 ppm by mass, preferably not more than 1.00 ppm by mass, more preferably not more than 0.90 ppm by mass, further preferably not more than 0.80 ppm by mass, and particularly preferably not more than 0.70 ppm by mass (e.g. not more than 0.60 ppm by mass). The lower limit of crotonaldehyde concentration in the second acetic acid stream may be, for example, 0.01 ppm by mass or 0.05 ppm by mass. The 2-ethyl crotonaldehyde concentration in the second acetic acid stream is, for example, not more than 0.80 ppm by mass, preferably not more than 0.70 ppm by mass, more preferably not more than 0.60 ppm by mass, further preferably not more than 0.50 ppm by mass, and particularly preferably not more than 0.40 ppm by mass. The lower limit of 2-ethyl crotonaldehyde concentration in the second acetic acid stream may be, for example, 0.01 ppm by mass or 0.05 ppm by mass. The propionic acid concentration in the second acetic acid stream is, for example, not more than 130 ppm by mass, preferably not more than 120 ppm by mass, more preferably not more than 110 ppm by mass, and further preferably not more than 80.0 ppm by mass. The lower limit of propionic acid concentration in the second acetic acid stream may be, for example, 1.0 ppm by mass, or 5.0 ppm by mass or 10.0 ppm by mass. The hexyl iodide concentration in the second acetic acid stream is, for example, not more than 30 ppb by mass, preferably not more than 25 ppb by mass, more preferably not more than 20 ppb by mass, further preferably not more than 17 ppb by mass, and particularly preferably not more than 10 ppb by mass. The lower limit of hexyl iodide concentration in the second acetic acid stream may be, for example, 0.1 ppb by mass (or 1.0 ppb by mass).

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. In this embodiment, the third distillation step is not an indispensable step. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, -100 to 150 kPa (gauge pressure), and the column bottom pressure is higher than the column top pressure and is set to, for example, -90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled from the condenser 6a through the lines 40, 41 and 42 to the first acetic acid stream in the line 27 before introduction to the distillation column 5. Together with this or instead of this, a portion (distillate) of the condensate portion may be recycled from the condenser 6a through the lines 40, 41 and 43 to the vapor stream in the line 21 before introduction to the distillation column 3. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 through the line 39 contains a larger amount of components having a higher boiling point (higher boiling point components) than that of acetic acid as compared with the overhead stream from the distillation column 6 and contains acetate, for example, propionate and potassium acetate (in the case of feeding alkali such as potassium hydroxide to the line 34, etc.). Also, the bottom fraction withdrawn from the column bottom of the distillation column 6 through the line 39 also contains, for example, a corroded metal such as a metal formed at and released from the inside wall of a member constituting this acetic acid production apparatus, and a compound composed of iodine derived from corrosive iodine and the corroded metal, etc. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.800 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. In particular, since the present invention provides acetic acid having a very high potassium permanganate test value by the evaporation treatment in the evaporator 5, the distillation column 6 can be omitted.

The ion exchange resin column 7 is a purification unit for performing the adsorptive removal step. This adsorptive removal step is a step for further purifying acetic acid by adsorptive removal of, mainly, alkyl iodides (e.g. ethyl iodide, propyl iodide, butyl iodide, hexyl iodide, decyl iodide, etc.) contained in a very small amount in the third acetic acid stream continuously introduced to the ion exchange resin column 7. The distillation column 6 may be omitted to feed the second acetic acid stream from the distillation column 5 to the ion exchange resin column 7. In addition, the adsorptive removal step using the ion exchange resin column 7 is not necessarily disposed.

In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per m$^3$ resin volume (m$^3$/h)] is, for example, 3 to 15 m$^3$/h·m$^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.900 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.900 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

EXAMPLES

Hereinafter, the present invention will be described in more detail with reference to Examples. However, the present invention is not intended to be limited by these Examples. The units "parts", "%", "ppm" and "ppb" are all based on mass. The water concentration was measured by the Karl Fischer water determination method; the metal concentration was measured by ICP analysis (or atomic adsorption analysis); and the concentrations of other components were measured by gas chromatography.

Comparative Example 1

The following experiments were conducted in a methanol method acetic acid pilot plant (cf. FIG. 1). Four hundred parts of reaction mixture liquid [composition: 7.6% of methyl iodide (MeI), 4.5% of methyl acetate (MA), 2.5% of water (H$_2$O), 910 ppm of rhodium complex (in terms of rhodium), 14.1% of lithium iodide (LiI), 212 ppm of acetaldehyde (AD), 2.0 ppm of crotonaldehyde (CR), 2.2 ppm of 2-ethyl crotonaldehyde (2ECR), 280 ppm of propionic acid, and acetic acid as a balance (however, a very small amount of impurities are contained)] obtained in a reaction vessel [a total pressure of 2.8 MPa (absolute pressure), a carbon monoxide partial pressure of 1.4 MPa (absolute pressure), a hydrogen partial pressure of 0.5 MPa (absolute pressure), a reaction temperature of 187° C.] were fed to an evaporator, and the evaporator was heated to evaporate 25% (evaporation rate: 25%). The acetaldehyde concentration in the evaporator bottom fraction was 73 ppm. One hundred parts of vapor of the evaporator [composition: 27.2% of methyl iodide, 14.7% of methyl acetate, 2.0% of water, 689 ppm of acetaldehyde, 2.8 ppm of crotonaldehyde, 0.60 ppm of 2-ethyl crotonaldehyde, 84.6 ppm of propionic acid, and acetic acid as a balance (however, a very small amount of impurities are contained)] were fed to a lower boiling point component removal column [20 actual plates, feed position: the second plate from the bottom, a column top pressure of 250 kPa (absolute pressure), a column top temperature of 140° C.] to condense the column top vapor. After separation into an aqueous phase and an organic phase in a decanter, a portion of the aqueous phase (11 parts) was sent to an acetaldehyde removal column [80 actual plates, feed position: the eleventh plate from the bottom, a column top pressure of 280 kPa (absolute pressure), a column top temperature of 52° C.] to separate and remove acetaldehyde to the outside of the system, and an aqueous solution (1.6 parts) after the acetaldehyde removal was recycled to the reaction system as a distillate liquid. The remaining portion of the aqueous phase was refluxed to the lower boiling point component removal column. The amount refluxed/amount of the distillate of the aqueous phase was refined as a reflux ratio, and the reflux ratio was set to 2. The organic phase (41 parts) was directly recycled to the reaction system. From the column bottom of the lower boiling point component removal column, 3 parts were withdrawn as a bottom fraction and recycled to the reaction system. From the middle part (the fourth plate from the bottom) of the lower boiling point component removal column, 65.7 parts were withdrawn as a side cut (SC) stream and fed to a dehydration column [50 actual plates, feed position: the thirty-fourth plate from the bottom, a column top pressure of 295 kPa (absolute pressure), a column top temperature of 150° C.] A portion of the column top vapor condensate of the dehydration column was refluxed (recycled) to the dehydration column, and the remaining portion (19 parts) was recycled to the reaction system as a distillate liquid. The reflux ratio (amount refluxed/amount of the distillate) of the dehydration column was set to 0.5. As a result, 46.7 parts of product acetic acid were obtained as a bottom fraction from the column bottom of the dehydration column. The amount of acetaldehyde removed (amount of AD removed) was 0.0141 parts, and the ratio of the amount of AD removed to the amount of dehydration column bottom fraction (amount of product produced) was $3.02 \times 10^{-4}$. In the product acetic acid, the crotonaldehyde content was 1.28 ppm, the 2-ethyl crotonaldehyde content was 0.95 ppm, the propionic acid content was 150 ppm, and the hexyl iodide content was 36 ppb. The permanganic acid time (chameleon time) of the product acetic acid was measured as 40 minutes. The results are shown in Table 1.

Comparative Example 2

The same experiment as in Comparative Example 1 was conducted except that a reflux ratio of the lower boiling point component removal column was set to 10. With this change, composition of the reaction mixture liquid and vapor composition of the evaporator were changed. The results are shown in Table 1.

Example 1

The same experiment as in Comparative Example 2 was conducted except that an evaporation rate in an evaporator was set to 28%. With this change, composition of the reaction mixture liquid and vapor composition of the evaporator were changed. The results are shown in Table 1.

Example 2

The same experiment as in Comparative Example 2 was conducted except that an evaporation rate in an evaporator was set to 31%. With this change, composition of the reaction mixture liquid and vapor composition of the evaporator were changed. The results are shown in Table 1.

Example 3

The same experiment as in Comparative Example 2 was conducted except that an evaporation rate in an evaporator was set to 35%. With this change, composition of the reaction mixture liquid and vapor composition of the evaporator were changed. The results are shown in Table 1.

Example 4

The same experiment as in Comparative Example 2 was conducted except that an evaporation rate in an evaporator was set to 31% and a reflux ratio of the lower boiling point component removal column was set to 15. With this change, composition of the reaction mixture liquid and vapor composition of the evaporator were changed. The results are shown in Table 1.

In Table 1, "AD" represents acetaldehyde, "MeI" represents methyl iodide, "MA" represents methyl acetate, "AC" represents acetic acid, "CR" represents crotonaldehyde, "2ECR" represents 2-ethyl crotonaldehyde, "PA" represents propionic acid, and "HexI" represents hexyl iodide. In Table 1, the numerical value in the column of each component represents a concentration.

TABLE 1

|  |  | Comparative Example | | Example | | | |
|---|---|---|---|---|---|---|---|
|  |  | 1 | 2 | 1 | 2 | 3 | 4 |
| Evaporator evaporation rate (%) | | 25 | 25 | 28 | 31 | 35 | 31 |
| Reflux ratio of lower boiling point component removal column | | 2 | 10 | 10 | 10 | 10 | 15 |
| Reaction mixture liquid | AD (ppm) | 212 | 212 | 209 | 205 | 203 | 194 |
|  | MeI (%) | 7.6 | 7.6 | 7.6 | 7.6 | 7.6 | 7.6 |
|  | MA (%) | 4.5 | 4.5 | 4.5 | 4.5 | 4.5 | 4.5 |
|  | H$_2$O (%) | 2.5 | 2.5 | 2.5 | 2.5 | 2.5 | 2.5 |
|  | CR (ppm) | 2.0 | 1.8 | 1.3 | 0.8 | 0.6 | 0.5 |
|  | 2ECR (ppm) | 2.2 | 1.9 | 1.0 | 0.7 | 0.4 | 0.3 |
|  | PA (ppm) | 280 | 251 | 213 | 213 | 209 | 140 |
| Evaporator bottom fraction | AD (ppm) | 73 | 73 | 58 | 36 | 20 | 34 |
| Feeding to lower boiling point component removal column | AD (ppm) | 689 | 689 | 597 | 581 | 543 | 550 |
|  | MeI (%) | 27.2 | 27.2 | 24.7 | 22.7 | 20.3 | 22.7 |
|  | MA (%) | 14.7 | 14.7 | 13.2 | 12.1 | 10.8 | 12.1 |
|  | H$_2$O (%) | 2.0 | 2.0 | 2.8 | 3.2 | 3.5 | 3.5 |
|  | AC (%) | 56.1 | 56.1 | 59.1 | 61.9 | 65.3 | 61.7 |

TABLE 1-continued

|  |  | Comparative Example | | Example | | | |
| --- | --- | --- | --- | --- | --- | --- | --- |
|  |  | 1 | 2 | 1 | 2 | 3 | 4 |
| Decanter aqueous phase | CR (ppm) | 2.8 | 2.5 | 1.7 | 1.0 | 0.7 | 0.6 |
|  | 2ECR (ppm) | 0.60 | 0.48 | 0.36 | 0.31 | 0.21 | 0.10 |
|  | PA (ppm) | 84.6 | 75.8 | 63.2 | 61.1 | 60.0 | 42.0 |
|  | AD (ppm) | 2330 | 2330 | 2470 | 2630 | 2810 | 2720 |
|  | MeI (%) | 3.2 | 3.2 | 3.5 | 3.6 | 3.2 | 3.2 |
|  | MA (%) | 19.0 | 19.0 | 18.1 | 17.3 | 16.5 | 16.7 |
|  | $H_2O$ (%) | 68.6 | 68.6 | 69.3 | 70.1 | 71.8 | 71.8 |
|  | AC (%) | 9.0 | 9.0 | 8.9 | 8.7 | 8.2 | 8.0 |
| Decanter organic phase | AD (ppm) | 1160 | 1160 | 1080 | 1140 | 1130 | 1090 |
|  | MeI (%) | 59.8 | 59.8 | 61.6 | 63.2 | 65.0 | 64.7 |
|  | MA (%) | 38.0 | 38.0 | 36.2 | 34.6 | 33.0 | 33.4 |
|  | $H_2O$ (%) | 0.6 | 0.6 | 0.6 | 0.6 | 0.6 | 0.6 |
|  | AC (%) | 1.5 | 1.5 | 1.5 | 1.5 | 1.3 | 1.2 |
| AD Distribution coefficient [aqueous phase (%)/ organic phase (%)] |  | 2.01 | 2.01 | 2.29 | 2.31 | 2.49 | 2.50 |
| Lower boiling point component removal column side cut liquid | CR (ppm) | 1.50 | 1.35 | 0.99 | 0.63 | 0.49 | 0.39 |
|  | 2ECR (ppm) | 0.72 | 0.62 | 0.47 | 0.41 | 0.28 | 0.18 |
|  | PA (ppm) | 120 | 108 | 88.7 | 83.9 | 78.6 | 58.9 |
| Dehydration column bottom fraction (product) | CR (ppm) | 1.28 | 1.15 | 0.84 | 0.53 | 0.42 | 0.33 |
|  | 2ECR (ppm) | 0.95 | 0.82 | 0.63 | 0.54 | 0.37 | 0.23 |
|  | PA (ppm) | 150 | 135 | 112 | 110 | 103 | 72.0 |
|  | HexI (ppb) | 36 | 31 | 23 | 19 | 18 | 15 |
| Amount of product produced (parts) |  | 46.7 | 46.7 | 47.5 | 48.9 | 51.3 | 48.4 |
| Amount of AD removed (parts) |  | 0.0141 | 0.0157 | 0.0167 | 0.0178 | 0.0190 | 0.0184 |
| Amount of AD removed/ Amount of product produced ($\times 10^{-4}$) |  | 3.02 | 3.36 | 3.51 | 3.63 | 3.70 | 3.80 |
| Product chameleon time (minute) |  | 40 | 90 | 120 | 140 | 145 | 160 |

[Discussion on Results]

From comparison of Comparative Example 2 and Examples 1 to 3, it is evident that when an evaporation rate is raised by heating the evaporator, and the AD concentration of the evaporator bottom fraction is decreased, and feed composition of the lower boiling point component removal column is changed, the AD concentration in a decanter is increased and the MA concentration of the decanter is kept below a certain value to thereby increase an AD distribution coefficient [aqueous phase AD concentration (o)/organic phase AD concentration (%)] and, as a result, AD removal efficiency goes up and the AD concentration in the reaction vessel is lowered to decrease the amounts of CR, 2ECR, HexI and PA generated and to raise product chameleon time.

From comparison of Comparative Examples 1 and 2 and Examples 2 and 4, it is evident that even in case of the same evaporation rate of the evaporator, when a reflux ratio of the lower boiling point component removal column is raised, AD removal efficiency goes up and the AD concentration in the reaction vessel is lowered to decrease the amounts of CR, 2ECR, HexI and PA generated and to raise product chameleon time.

From the above, it is evident that when the evaporator is heated to raise the AD concentration in the column top decanter of the lower boiling point component removal column or to lower the MA concentration and when a reflux ratio of the lower boiling point component removal column is also raised, AD removal efficiency is increased to improved product quality.

In conclusion, the composition of the present invention and its variation are appended below.

[1] A method for producing acetic acid, comprising: a carbonylation reaction step of reacting methanol with carbon monoxide in a reaction vessel in the presence of a catalyst system containing a metal catalyst and methyl iodide as well as acetic acid, methyl acetate, and water to produce acetic acid;

an evaporation step of introducing and heating a reaction mixture obtained at the carbonylation reaction step in an evaporator to separate the reaction mixture into a vapor stream and a residual liquid stream;

a residual liquid stream recycle step of recycling the residual liquid stream to the reaction vessel;

a lower boiling point component removal step of separating the vapor stream with a first distillation column into a first overhead stream rich in methyl iodide and acetaldehyde and a first acetic acid stream rich in acetic acid and of condensing and separating the first overhead stream to obtain a aqueous phase and an organic phase;

a first overhead stream recycle step of recycling at least a portion of the aqueous phase and/or the organic phase to the reaction vessel; and an acetaldehyde separation and removal step of separating and removing acetaldehyde in a process stream, wherein with heating of the evaporator, (i) an acetaldehyde concentration in the aqueous phase is controlled to not less than 2340 ppm by mass; and/or (ii) a methyl acetate concentration in the aqueous phase is controlled to less than 19.0% by mass and/or; (iii) a methyl acetate concentration in the organic phase is controlled to less than 38.0% by mass, and then at least a portion of the aqueous phase is treated in the acetaldehyde separation and removal step to recycle a residual liquid after the acetaldehyde separation and removal to the reaction vessel and/or the acetaldehyde separation and removal step and/or other processes.

[2] The method for producing acetic acid according to [1], wherein the catalyst system further contains an ionic iodide.

[3] The method for producing acetic acid according to [1] or [2], wherein with regard to operation conditions of the first distillation column, when only the aqueous phase is refluxed to the first distillation column, a reflux ratio of the aqueous phase is not less than 2 (preferably not less than 3, more preferably not less than 5, further preferably not less than 8, particularly preferably not less than 10 and, in particular, not less than 12); when only the organic phase is refluxed, a reflux ratio of the organic phase is not less than 1 (preferably not less than 1.5, more preferably not less than 2, further preferably not less than 4, and particularly preferably not less than 5); and when both the aqueous and organic phases are refluxed, a total reflux ratio of the aqueous and organic phases is not less than 1.5 (preferably not less than 2.3, more preferably not less than 3.5, further preferably not less than 6, and particularly preferably not less than 8.5).

[4] The method for producing acetic acid according to any one of [1] to [3], wherein the method further comprises a dehydration step of separating the first acetic acid stream with a second distillation column into a second overhead stream rich in water and a second acetic acid stream more enriched with acetic acid than the first acetic acid stream.

[5] The method for producing acetic acid according to [4], wherein in the second acetic acid stream, a crotonaldehyde concentration is not more than 1.10 ppm by mass (preferably not more than 1.00 ppm by mass, more preferably not more than 0.90 ppm by mass, further preferably not more than 0.80 ppm by mass, particularly preferably not more than 0.70 ppm by mass and, in particular, not more than 0.60 ppm by mass); and/or a 2-ethyl crotonaldehyde concentration is not more than 0.80 ppm by mass (preferably not more than 0.70 ppm by mass, more preferably not more than 0.60 ppm by mass, further preferably not more than 0.50 ppm by mass, and particularly preferably not more than 0.40 ppm by mass); and/or a propionic acid concentration is not more than 130 ppm by mass (preferably not more than 120 ppm by mass, more preferably not more than 110 ppm by mass, and further preferably not more than 80.0 ppm by mass).

[6] The method for producing acetic acid according to [4] or [5], wherein a hexyl iodide concentration in the second acetic acid stream is not more than 30 ppb by mass (preferably not more than 25 ppb by mass, more preferably not more than 20 ppb by mass, further preferably not more than 17 ppb by mass, and particularly preferably not more than 10 ppb by mass).

[7] The method for producing acetic acid according to any one of [1] to [6], wherein an acetaldehyde concentration in the residual liquid stream in the evaporator is set to not more than 70 ppm by mass (more preferably not more than 60 ppm by mass, more preferably not more than 50 ppm by mass, further preferably not more than 40 ppm by mass, and particularly preferably not more than 30 ppm by mass).

[8] The method for producing acetic acid according to any one of [1] to [7], wherein in the reaction mixture liquid of the reaction vessel, a crotonaldehyde concentration is not more than 1.7 ppm by mass (preferably not more than 1.4 ppm by mass, more preferably not more than 1.2 ppm by mass, further preferably not more than 1.0 ppm by mass, particularly preferably, not more than 0.8 ppm by mass and, in particular, not more than 0.6 ppm by mass); and/or a 2-ethyl crotonaldehyde concentration is not more than 1.8 ppm by mass (preferably not more than 1.6 ppm by mass, more preferably not more than 1.4 ppm by mass, further preferably not more than 1.2 ppm by mass, particularly preferably more than 1.0 ppm by mass and, in particular, not more than 0.8 ppm by mass); and/or a propionic acid concentration is not more than 240 ppm by mass (preferably not more than 230 ppm by mass, more preferably not more than 220 ppm by mass, further preferably not more than 200 ppm by mass, and particularly preferably not more than 180 ppm by mass).

[9] The method for producing acetic acid according to any one of [1] to [8], wherein in the vapor stream fed to the first distillation column, a crotonaldehyde concentration is not more than 2.4 ppm by mass (preferably not more than 2.2 ppm by mass, more preferably not more than 2.0 ppm by mass, further preferably not more than 1.6 ppm by mass, and particularly preferably not more than 1.2 ppm by mass); and/or a 2-ethyl crotonaldehyde concentration is not more than 0.45 ppm by mass (preferably not more than 0.40 ppm by mass, more preferably not more than 0.30 ppm by mass); and/or a propionic acid concentration is not more than 106 ppm by mass (preferably not more than 74.0 ppm by mass, more preferably not more than 65.0 ppm by mass, and further preferably not more than 55.0 ppm by mass).

[10] The method for producing acetic acid according to any one of [1] to [9], wherein in the first acetic acid stream, a crotonaldehyde concentration is not more than 1.34 ppm by mass (preferably not more than 1.20 ppm by mass, more preferably not more than 1.00 ppm by mass, further preferably not more than 0.80 ppm by mass, and particularly preferably not more than 0.60 ppm by mass); and/or a 2-ethyl crotonaldehyde concentration is not more than 0.60 ppm by mass (preferably not more than 0.50 ppm by mass, more preferably not more than 0.40 ppm by mass); and/or a propionic acid concentration is not more than 106 ppm by mass (preferably not more than 100 ppm by mass, more preferably not more than 90.0 ppm by mass, and further preferably not more than 80.0 ppm by mass).

[11] A method for producing acetic acid, comprising: a carbonylation reaction step of reacting methanol with carbon monoxide in a reaction vessel in the presence of a catalyst system containing a metal catalyst and methyl iodide as well as acetic acid, methyl acetate, and water to produce acetic acid;

an evaporation step of introducing and heating a reaction mixture obtained in the carbonylation reaction step in an evaporator to separate the reaction mixture into a vapor stream and a residual liquid stream;

a residual liquid stream recycle step of recycling the residual liquid stream to the reaction vessel;

a lower boiling point component removal step of separating the vapor stream with a first distillation column into a first overhead stream rich in methyl iodide and acetaldehyde and a first acetic acid stream rich in acetic acid and of condensing and separating the first overhead stream to obtain an aqueous phase and an organic phase;

a first overhead stream recycle step of recycling at least a portion of the aqueous phase and/or the organic phase to the reaction vessel; and an acetaldehyde separation and removal step of separating and removing acetaldehyde in a process stream, wherein with heating of the evaporator, (i) an acetaldehyde concentration in the aqueous phase is controlled to not less than 2340 ppm by mass; and/or (ii) a methyl acetate concentration in the aqueous phase is controlled to less than 19.0% by mass; and/or (iii) a methyl acetate concentration in the organic phase is controlled to less than 38.0% by mass, and an acetaldehyde concentration in the residual liquid stream is controlled to not more than 70 ppm by mass; at least a portion of the aqueous phase is treated in the acetaldehyde separation and removal step to recycle a residual liquid after the acetaldehyde separation and removal to the reaction vessel and/or the acetaldehyde separation and removal step and/or other processes; and a reflux ratio of the aqueous phase of the first distillation column is not less than 2.

[12] The method for producing acetic acid according to [11], wherein the catalyst system further contains an ionic iodide.

[13] The method for producing acetic acid according to [11] or [12], wherein a reflux ratio of the aqueous phase is not less than 3 (preferably not less than 5, more preferably not less than 8, further preferably not less than 10, and particularly preferably not less than 12).

[14] The method for producing acetic acid according to any one of [11] to [13], wherein the method further comprise a dehydration step of separating the first acetic acid stream with a second distillation column into a second overhead stream rich in water and a second acetic acid stream more enriched with acetic acid than the first acetic acid stream.

[15] The method for producing acetic acid according to [14], wherein in the second acetic acid stream, a crotonaldehyde concentration is not more than 1.10 ppm by mass (preferably not more than 1.00 ppm by mass, more preferably not more than 0.90 ppm by mass, further preferably not more than 0.80 ppm by mass, particularly preferably not more than 0.70 ppm by mass and, in particular, not more than 0.60 ppm by mass); and/or a 2-ethyl crotonaldehyde concentration is not more than 0.80 ppm by mass (preferably not more than 0.70 ppm by mass, more preferably not more than 0.60 ppm by mass, further preferably not more than 0.50 ppm by mass, and particularly preferably not more than 0.40 ppm by mass); and/or a propionic acid concentration is not more than 130 ppm by mass (preferably not more than 120 ppm by mass, more preferably not more than 110 ppm by mass, and further preferably not more than 80.0 ppm by mass).

[16] The method for producing acetic acid according to [14] or [15], wherein a hexyl iodide concentration in the second acetic acid stream is not more than 30 ppb by mass (preferably not more than 25 ppb by mass, more preferably not more than 20 ppb by mass, further preferably not more than 17 ppb by mass, and particularly preferably not more than 10 ppb by mass).

[17] The method for producing acetic acid according to any one of [11] to [16], wherein an acetaldehyde concentration in the residual liquid stream in the evaporator is set to not more than 60 ppm by mass (preferably not more than 50 ppm by mass, more preferably not more than 40 ppm by mass, and further preferably not more than 30 ppm by mass).

[18] The method for producing acetic acid according to any one of [11] to [17], wherein in the reaction mixture liquid of the reaction vessel, a crotonaldehyde concentration is not more than 1.7 ppm by mass (preferably not more than 1.4 ppm by mass, more preferably not more than 1.2 ppm by mass, further preferably not more than 1.0 ppm by mass, particularly preferably not more than 0.8 ppm by mass and, in particular, not more than 0.6 ppm by mass); and/or a 2-ethyl crotonaldehyde concentration is not more than 1.8 ppm by mass (preferably not more than 1.6 ppm by mass, more preferably not more than 1.4 ppm by mass, further preferably not more than 1.2 ppm by mass, particularly preferably more than 1.0 ppm by mass and, in particular, not more than 0.8 ppm by mass); and/or a propionic acid concentration is not more than 240 ppm by mass (preferably not more than 230 ppm by mass, more preferably not more than 220 ppm by mass, further preferably not more than 200 ppm by mass, and particularly preferably not more than 180 ppm by mass).

[19] The method for producing acetic acid according to any one of [11] to [18], wherein in the vapor stream fed to the first distillation column, a crotonaldehyde concentration is not more than 2.4 ppm by mass (preferably not more than 2.2 ppm by mass, more preferably not more than 2.0 ppm by mass, further preferably not more than 1.6 ppm by mass, and particularly preferably not more than 1.2 ppm by mass); and/or a 2-ethyl crotonaldehyde concentration is not more than 0.45 ppm by mass (preferably not more than 0.40 ppm by mass, more preferably not more than 0.30 ppm by mass); and/or a propionic acid concentration is not more than 106 ppm by mass (preferably not more than 74.0 ppm by mass, more preferably not more than 65.0 ppm by mass, and further preferably not more than 55.0 ppm by mass).

[20] The method for producing acetic acid according to any one of [11] to [19], wherein in the first acetic acid stream, a crotonaldehyde concentration is not more than 1.34 ppm by mass (preferably not more than 1.20 ppm by mass, more preferably not more than 1.00 ppm by mass, further preferably not more than 0.80 ppm by mass, and particularly preferably not more than 0.60 ppm by mass); and/or a 2-ethyl crotonaldehyde concentration is not more than 0.60 ppm by mass (preferably not more than 0.50 ppm by mass, more preferably not more than 0.40 ppm by mass); and/or. a propionic acid concentration is not more than 106 ppm by mass (preferably not more than 100 ppm by mass, more preferably not more than 90.0 ppm by mass, and further preferably not more than 80.0 ppm by mass).

[21] The method for producing acetic acid according to any one of [11] to [20], wherein in the above-mentioned (i), an acetaldehyde concentration in the aqueous phase is not less than 2400 ppm by mass (preferably not less than 2500 ppm by mass and more preferably not less than 2600 ppm by mass).

[22] The method for producing acetic acid according to any one of [11] to [21], wherein in the above-mentioned (ii), a methyl acetate concentration in the aqueous phase is not more than 18.5% by mass (preferably not more than 17.5% by mass and more preferably not more than 17.0% by mass).

[23] The method for producing acetic acid according to any one of [11] to [22], wherein in the above-mentioned (iii), a methyl acetate concentration in the organic phase is not more than 37.5% by mass (preferably not more than 37.0% by mass, more preferably not more than 35.0% by mass, further preferably not more than 30.0% by mass, and particularly preferably not more than 25.0% by mass).

[24] The method for producing acetic acid according to any one of [11] to [23], wherein in the above-mentioned (iii), the lower limit of methyl acetate concentration in the organic phase is 1.0% by mass (preferably 2.0% by mass, more preferably 5.0% by mass, further preferably 10.0% by mass, particularly preferably 15.0% by mass and, in particular, 20.0% by mass).

[25] The method for producing acetic acid according to any one of [11] to [24], wherein an acetaldehyde concentration in the reaction mixture liquid of the reaction vessel is not more than 500 ppm by mass (preferably not more than 450 ppm by mass, more preferably not more than 400 ppm by mass, further preferably not more than 350 ppm by mass, particularly preferably not more than 300 ppm by mass, in particular not more than 250 ppm by mass, and most preferably not more than 210 ppm by mass).

INDUSTRIAL AVAILABILITY

The method for producing acetic acid according to the present invention can be used as an industrial method for producing acetic acid by the methanol method carbonylation process (methanol method acetic acid process).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:

1. A method for producing acetic acid, comprising:
a carbonylation reaction step of reacting methanol with carbon monoxide in a reaction vessel in the presence of a catalyst system containing a metal catalyst and methyl iodide as well as acetic acid, methyl acetate, and water to produce acetic acid;
an evaporation step of introducing and heating a reaction mixture obtained in the carbonylation reaction step in an evaporator to separate the reaction mixture into a vapor stream and a residual liquid stream;
a residual liquid stream recycle step of recycling the residual liquid stream to the reaction vessel;
a lower boiling point component removal step of separating the vapor stream with a first distillation column into a first overhead stream rich in methyl iodide and acetaldehyde and a first acetic acid stream rich in acetic acid and of condensing and separating the first overhead stream to obtain an aqueous phase and an organic phase;
a first overhead stream recycle step of recycling at least a portion of the aqueous phase and/or the organic phase to the reaction vessel; and
an acetaldehyde separation and removal step of separating and removing acetaldehyde in a process stream,
wherein the ratio between the vapor stream and the residual liquid stream to be separated in the evaporation step is 28/72 to 60/40 in terms of a mass ratio wherein evaporation rate is 28 to 60% by mass,
wherein with regard to operation conditions of the first distillation column, when only the aqueous phase is refluxed to the first distillation column, a reflux ratio of the aqueous phase is not less than 2; when only the organic phase is refluxed, a reflux ratio of the organic phase is not less than 1; and when both the aqueous and organic phases are refluxed, a total reflux ratio of the aqueous and organic phases is not less than 1.5, and
wherein with heating of the evaporator, (i) an acetaldehyde concentration in the aqueous phase is controlled to not less than 2340 ppm by mass; (ii) a methyl acetate concentration in the aqueous phase is controlled to less than 19.0% by mass; and (iii) a methyl acetate concentration in the organic phase is controlled to less than 38.0% by mass, and at least a portion of the aqueous phase is treated in the acetaldehyde separation and removal step to recycle a residual liquid after the acetaldehyde separation and removal to the reaction vessel and/or the acetaldehyde separation and removal step and/or other processes.

2. The method for producing acetic acid according to claim 1, wherein the catalyst system further contains an ionic iodide.

3. The method for producing acetic acid according to claim 1, further comprising a dehydration step of separating the first acetic acid stream with a second distillation column into a second overhead stream rich in water and a second acetic acid stream more enriched with acetic acid than the first acetic acid stream.

4. The method for producing acetic acid according to claim 3, wherein in the second acetic acid stream, a crotonaldehyde concentration is not more than 1.10 ppm by mass; and/or a 2-ethyl crotonaldehyde concentration is not more than 0.80 ppm by mass; and/or a propionic acid concentration is not more than 130 ppm by mass.

5. The method for producing acetic acid according to claim 1, wherein an acetaldehyde concentration in the residual liquid stream in the evaporator is set to not more than 70 ppm by mass.

6. The method for producing acetic acid according to claim 1, wherein in the reaction mixture liquid of the reaction vessel, a crotonaldehyde concentration is not more than 1.7 ppm by mass; and/or a 2-ethyl crotonaldehyde concentration is not more than 1.8 ppm by mass; and/or a propionic acid concentration is not more than 240 ppm by mass.

7. The method for producing acetic acid according to claim 1, wherein in the vapor stream fed to the first distillation column, a crotonaldehyde concentration is not more than 2.4 ppm by mass; and/or a 2-ethyl crotonaldehyde concentration is not more than 0. 45 ppm by mass; and/or a propionic acid concentration is not more than 106 ppm by mass.

8. The method for producing acetic acid according to claim 1, wherein in the first acetic acid stream, a crotonaldehyde concentration is not more than 1.34 ppm by mass; and/or a 2-ethyl crotonaldehyde concentration is not more than 0.60 ppm by mass; and/or a propionic acid concentration is not more than 106 ppm by mass.

9. A method for producing acetic acid, comprising:
- a carbonylation reaction step of reacting methanol with carbon monoxide in a reaction vessel in the presence of a catalyst system containing a metal catalyst and methyl iodide as well as acetic acid, methyl acetate, and water to produce acetic acid;
- an evaporation step of introducing and heating a reaction mixture obtained in the carbonylation reaction step in an evaporator to separate the reaction mixture into a vapor stream and a residual liquid stream;
- a residual liquid stream recycle step of recycling the residual liquid stream to the reaction vessel;

a lower boiling point component removal step of separating the vapor stream with a first distillation column into a first overhead stream rich in methyl iodide and acetaldehyde and a first acetic acid stream rich in acetic acid and of condensing and separating the first overhead stream to obtain an aqueous phase and an organic phase;
- a first overhead stream recycle step of recycling at least a portion of the aqueous phase and/or the organic phase to the reaction vessel; and an acetaldehyde separation and removal step of separating and removing acetaldehyde in a process stream,
wherein the ratio between the vapor stream and the residual liquid stream to be separated in the evaporation step is 28/72 to 60/40 in terms of a mass ratio wherein evaporation rate is 28 to 60% by mass, and
wherein with heating of the evaporator, (i) an acetaldehyde concentration in the aqueous phase is controlled to not less than 2340 ppm by mass; (ii) a methyl acetate concentration in the aqueous phase is controlled to not more than 17.5% by mass; and (iii) a methyl acetate concentration in the organic phase is controlled to not more than 35.0% by mass, and an acetaldehyde concentration in the residual liquid stream is controlled to not more than 70 ppm by mass; at least a portion of the aqueous phase is treated in the acetaldehyde separation and removal step to recycle a residual liquid after the acetaldehyde separation and removal to the reaction vessel and/or the acetaldehyde separation and removal step and/or other processes; and a reflux ratio of the aqueous phase of the first distillation column is not less than 2.

10. The method for producing acetic acid according to claim 9, wherein the catalyst system further contains an ionic iodide.

* * * * *